United States Patent [19]

Million et al.

[11] 4,160,082

[45] Jul. 3, 1979

[54] INTERMEDIATES FOR AMINOGLYCOSIDE ANTIBIOTICS

[75] Inventors: William A. Million, Ramsgate; Rhona M. Plews; Kenneth Richardson, both of Canterbury, all of England

[73] Assignee: Pfizer Inc., New York, N.Y.

[21] Appl. No.: 851,400

[22] Filed: Nov. 14, 1977

Related U.S. Application Data

[63] Continuation-in-part of Ser. No. 784,979, Apr. 6, 1977, abandoned.

[30] Foreign Application Priority Data

Apr. 14, 1976 [GB] United Kingdom ............... 15421/76

[51] Int. Cl.² .................... C07H 15/22; C07G 11/00
[52] U.S. Cl. .................................... 536/10; 536/17 R; 424/180
[58] Field of Search .............................. 536/10, 17, 4

[56] References Cited

U.S. PATENT DOCUMENTS

| | | | |
|---|---|---|---|
| 3,781,268 | 12/1973 | Kawaguchi et al. | 536/10 |
| 3,904,597 | 9/1975 | Naito et al. | 536/10 |
| 4,001,208 | 1/1977 | Umezawa et al. | 536/10 |
| 4,065,615 | 12/1977 | Horii et al. | 536/10 |

*Primary Examiner*—Johnnie R. Brown
*Assistant Examiner*—Blondel Hazel
*Attorney, Agent, or Firm*—Connolly and Hutz

[57] ABSTRACT

Derivatives of kanamycin A, which have an acyl protecting group on the C-3″ and C-6′ amino groups, and optionally have a benzyl protecting group on the C-3 amino group, are useful intermediates for the preparation of 1-N-(ω-amino-2-hydroxyalkyl) derivatives of kanamycin A. Derivatives of kanamycin B, which have an acyl protecting group on the C-2′, C-3″ and C-6′ amino groups, and optionally have a benzyl protecting group on the C-3 amino group, are useful intermediates for the preparation of 1-N-(ω-amino-2-hydroxyalkyl) derivatives of kanamycin B. Certain of the partially protected kanamycin A and kanamycin B derivatives of this invention are useful for preparing 1-N-(ω-amino-2-hydroxyalkanoyl) derivatives of kanamycin A and B. 1-N-(ω-Amino-2-hydroxyalkyl) and 1-N-(ω-amino-2-hydroxyalkanoyl)derivatives of kanamycin A and B are known antibacterial agents.

11 Claims, No Drawings

INTERMEDIATES FOR AMINOGLYCOSIDE ANTIBIOTICS

CROSS-REFERENCE TO RELATED APPLICATIONS

This application is a continuation-in-part of application Ser. No. 784,979, filed Apr. 6, 1977 now abandoned.

BACKGROUND OF THE INVENTION

This invention relates to certain new chemical compounds and processes for their preparation. More particularly, this invention relates to certain selectively protected derivatives of kanamycins A and B, and processes therefor, said selectively protected derivatives being of value as intermediates for the preparation of known antibacterial agents. Known antibacterial agents for which the selectively protected derivatives of kanamycin A and B of this invention are of use are kanamycins A and B having an ω-amino-2-hydroxyalkyl group on the 1-amino group. Additionally, certain of the selectively protected kanamycin A and kanamycin B derivatives of this invention are of use as intermediates to kanamycins A and B having an ω-amino-2-hydroxyalkanoyl group on the 1-amino group.

Preparation of 1-N-(ω-amino-2-hydroxyalkanoyl) derivatives of kanamycins A and B, via acylation of kanamycins A and B, or selectively protected derivatives thereof, are described in U.S. Pat. Nos. 3,781,268, 3,886,139, 3,904,597 and 3,974,137. Reduction of 1-N-(ω-amino-2-hydroxyalkanoyl) derivatives of kanamycins A and B to the corresponding 1-N-(ω-amino-2-hydroxyalkyl) compound is described in West German Offenlegungsschrift 2,547,738.

Belgian Pat. No. 817,546 describes the preparation of 3,3'',6'-tri-N-formylkanamycin A and 2',3,3'',6'-tetra-N-formylkanamycin B. Pending U.S. patent application Ser. No. 767,657, and Belgian Pat. No. 851,777, broadly disclose the use of selectively protected kanamycin derivatives, including 3,3'',6'-tri-N-formylkanamycin A and 2',3,3'',6'-tetra-N-formylkanamycin B, for the preparation of 1-N-(ω-amino-2-hydroxyalkyl) derivatives of kanamycins A and B. However, none of these references specifically identifies nor specifically teaches how to make the selectively protected kanamycin A and B derivatives of the present invention.

SUMMARY OF THE INVENTION

According to the invention there are provided novel compounds of the formula:

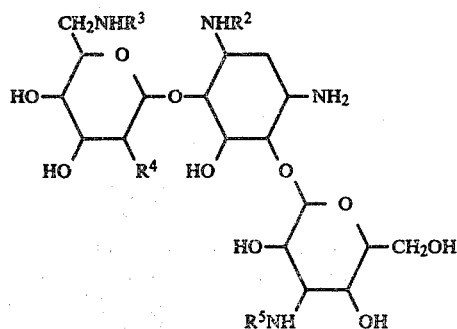

wherein $R^2$ is selected from the group consisting of hydrogen and benzyl;

$R^4$ is selected from the group consisting of hydroxy and $R^6NH$;

and $R^3$, $R^5$ and $R^6$ are each selected from the group consisting of formyl, alkanoyl having from 2 to 5 carbon atoms, fluoroacetyl, difluoroacetyl, trifluoroacetyl, chloroacetyl, dichloroacetyl, trichloroacetyl, alkoxycarbonyl having from 2 to 5 carbon atoms, and benzoyl;

provided that $R^3$, $R^5$ and $R^6$ are always the same.

Also, according to the invention, there is provided a first process. Said first process is for the production of a compound of the formula IA, wherein $R^2$ is as defined previously; $(R^4)'$ is selected from the group consisting of hydroxy and $(R^6)'NH$; and $(R^3)'$, $(R^5)'$ and $(R^6)'$ are selected from the group consisting of formyl, alkanoyl having from 2 to 5 carbon atoms, fluoroacetyl, difluoroacetyl, trifluoroacetyl, chloroacetyl, dichloroacetyl and trichloroacetyl; provided that $(R^3)'$, $(R^5)'$ and $(R^6)'$ are always the same.

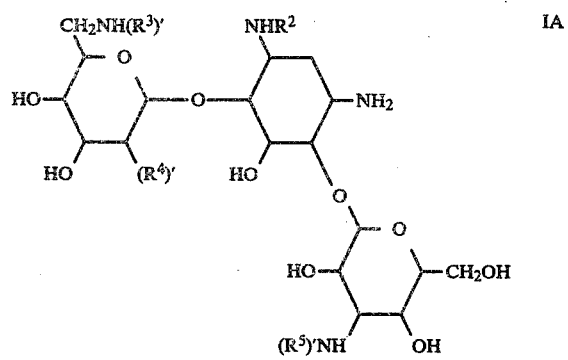

Said first process comprises the steps of:
(a) reacting a compound of the formula

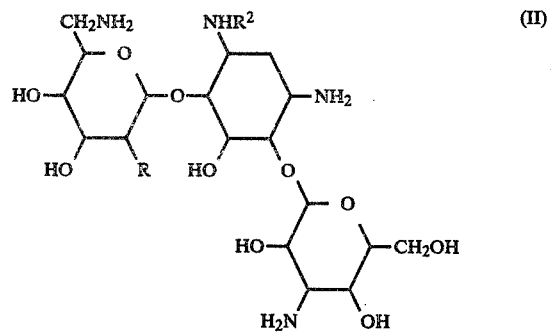

wherein R is selected from the group consisting of hydroxy and amino and $R^2$ is selected from the group consisting of hydrogen and benzyl, with an excess of formic-acetic anhydride or an activated derivative of a carboxylic acid of formula $R^7COOH$, in a reaction-inert solvent, at a pH below about 5, wherein $R^7$ is selected from the group consisting of alkyl having from 1 to 4 carbon atoms, fluoromethyl, difluoromethyl, trifluoromethyl, chloromethyl, dichloromethyl and trichloromethyl;

(b) neutralizing a solution of the product of step (a), in a reaction-inert organic solvent, and at a temperature of from about 0° to about 50° C.; and (c) hydrolyzing the product of step (b), at a temperature of from about 0° to about 100° C.

In step (a) of the above reaction sequence all the reactive hydroxy groups, but none of the amino groups, are acylated, and the term excess means at least a molar amount of the acylating agent which is sufficient to acylate all the reactive hydroxy groups. A variety of activated derivatives of the acid of the formula $R^7COOH$ can be used; however, the preferred activated derivatives are anhydrides of the formula $(R^7CO)_2O$.

Further, according to the invention, there is provided a second process. Said second process is for the preparation of a compound of the formula I, wherein $R^2$, $R^3$, $R^4$, $R^5$ and $R^6$ are as previously defined. Said second process comprises the steps of:

(i) reacting a compound of the formula

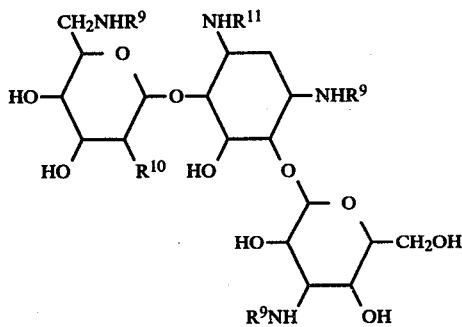

wherein $R^9$ is selected from the group consisting of benzyloxycarbonyl and t-butyloxycarbonyl; $R^{10}$ is selected from the group consisting of hydroxy and $NHR^9$; and $R^{11}$ is selected from the grooup consisting of benzyl and $R^9$, with an excess of formic-acetic anhydride, an activated derivative of a carboxylic acid of formula $(R^7)'COOH$ or a chloroformate of formula $R^8$—CO—Cl, in a reaction-inert solvent, wherein $(R^7)'$ is selected from the group consisting of alkyl from 1 to 4 carbon atoms, fluoromethyl, difluoromethyl, trifluoromethyl, chloromethyl, dichloromethyl, trichloromethyl and phenyl; and $R^8$ is alkoxy having from 1 to 4 carbon atoms;

(ii) removing the amino protecting groups;

(iii) neutralizing a solution of the product of step (ii), in a reaction-inert solvent, at a temperature of from about 0° to about 50° C.; and (iv) hydrolyzing the product of step (iii), at a temperature of from about 0° C. to about 100° C.

In step (i) of the above reaction sequence all the reactive hydroxy groups are acylated, and the term excess means at least a molar amount of the acylating agent which is sufficient to acylate all the reactive hydroxy groups. A variety of activated derivatives of the acid of the formula $(R^7)'COOH$ can be used; however, the preferred activated derivatives are anhydrides of the formula $[(R^7)'CO]_2O$ and acid chlorides of the formula $(R^7)'$—CO—Cl. The preferred group for $R^9$ is benzyloxycarbonyl.

DETAILED DESCRIPTION OF THE INVENTION

Step (a) of the said first process involves a selective O-acylation of a compound of the formula II. This is achieved by treating a compound of the formula II with an excess of formic-acetic anhydride or an activated derivative of a carboxylic acid of the formula $R^7COOH$, wherein $R^7$ is as defined previously. In order to achieve selective O-acylation the reaction is performed at a pH of less than about 5, in an appropriate reaction-inert solvent. A reaction-inert solvent is one which does not adversely interact with either the starting material of the formula II or its O-acylated product, and one in which the starting material of the formula II has a significant degree of solubility. In this regard, it is convenient to use a strongly acidic solvent such as trifluoroacetic acid.

In step (a), it is essential to use sufficient acylating agent to acylate all the reactive hydroxy groups in the compound of the formula II. In practice, in the case wherein R is hydroxy at least 5 molar equivalents of acylating agent should be used, and in the case wherein R is amino at least 4 molar equivalents of acylating agent should be used.

Step (b) of the aforementioned reaction reaction sequence involves an O→N acyl migration reaction, in which acyl groups migrate from an oxygen atom to the amino groups at C-3" and C-6', and to the amino group at C-2' if R is amino. This acyl migration is induced simply by neutralizing the product of step (a). In practice, the product of step (a) is usually isolated as an acid-addition salt, and this acid-addition salt is dissolved in a reaction-inert organic solvent and then the pH is raised to neutrality. The O→N acyl migration proceeds spontaneously. Although the O→N acyl migration can be carried out at a temperature from about 0° to about 50° C., it is usual to perform same at about 25° C. At 25° C. the O→ acyl migration is normally substantially complete within a few hours, e.g. 4 hours.

Step (c) of the aforementioned reaction sequence involves removal of any remaining O-acyl groups from the product of step (b). This is a conventional hydrolysis or alcoholysis reaction and it is carried out at a temperature of from about 0° to about 100° C. Generally, it is carried out in the presence of an acidic or a basic catalyst. When the hydrolysis is carried out in the presence of a basic catalyst, at least one molar equivalent of water is required and it is convenient to use a sufficiently large excess of water and a further diluent is not necessary. However, cosolvents which do not adversely interact with the reagents or products may be used. The lower alkanols are typical examples of such cosolvents and methanol and ethanol are preferred. The basic catalyst is normally present in the amount of at least one molar equivalent but much larger amounts, for example up to about 20 molar equivalents, may be used. Typical examples of the basic catalyst include ammonium hydroxide; alkali metal hydroxides such as sodium hydroxide and potassium hydroxide; alkaline earth metal hydroxides such as barium hydroxide and calcium hydroxide; and alkali metal carbonates such as sodium carbonate and potassium carbonate.

When hydrolysis is carried out in the presence of an acid catalyst, at least one molar equivalent of water, an alkanol having 1 to 5 carbon atoms or a mixture thereof is required and it is desirable to use an excess, preferably greater than about 5 molar equivalents, in order to achieve optimum yields. Generally, sufficient water, alkanol or a mixture thereof is used so that a further solvent is not required. However, a further solvent which is miscible with water, the alkanol or the water-alkanol mixture and which does not interact with the reagents or products may be used. Typical examples of such solvents include 1,2-dimethoxyethane, 1,2-diethoxyethane, dioxane, tetrahydrofuran, ethylene glycol, diethylene glycol, propylene glycol, ethylene glycol monomethyl ether, ethylene glycol monoethyl ether, diethylene glycol monomethyl ether, diethylene glycol monoethyl ether and diethylene glycol diethyl ether. The aforesaid alkanols containing 1 to 5 carbon atoms include both straight and branched chain alkanols such as methanol, ethanol and isopropanol. When a mixture of water and an alkanol is used, the ratio thereof can vary widely. However, it is usually convenient to choose ratios under which the medium is homogeneous.

As will be appreciated by one skilled in the art, step (c) is, in effect, a selective hydrolysis in that O-acyl groups are being removed while the N-acyl groups remain intact. Accordingly, the particular reaction conditions chosen for step (c) will depend on the particular acyl group $(R^3)'$,$(R^5)'$ and $(R^6)'$. When the acyl group is of the class that is easily hydrolyzed, mild hydrolyzing conditions will be selected; the more vigorous hydrolyzing conditions will only be used for the acyl group more difficultly hydrolyzable. In fact, when the acyl group is a particularly labile group, such as the trifluoroacetyl group, it is usually not necessary to use either a basic or an acidic catalyst.

If desired, a compound of the formula I, wherein $R^2$ is benzyl, can be converted into the corresponding compound wherein $R^2$ is hydrogen by hydrogenolysis. This is conveniently performed by dissolving said compound of the formula I, wherein $R^2$ is benzyl, in a suitable solvent, e.g. a mixture of methanol, water and acetic acid and subjecting the mixture to a conventional hydrogenation, e.g. at 50 p.s.i. and 40° C. in the presence of a palladium catalyst. Under these conditions the reaction is substantially complete within 14 hours. The product is isolated, after filtration, by evaporation of the solvent. Purification may then be achieved, if desired, by for example ion-exchange chromatography, to give the product in pure form.

In said second process, kanamcycin A or kanamycin B is first treated with a reagent to introduce selectively removable amino-blocking groups. Suitable blocking groups are, for example, the t-butyloxycarbonyl group or the benzyloxycarbonyl group. The fully N-protected product is then O-actylated by known techniques, for example by treatment with an excess of formic-acetic anhydride or a compound of the formula $[(R^7)'CO]_2$, $(R^7)'COCl$ or $R^8$—CO—Cl, wherein $(R^7)'$ and $R^8$ are as defined previously, and the amino blocking groups are then removed (e.g. the t-butyloxycarbonyl groups are removed by treatment with trifluoroacetic acid and the benzyloxycarbonyl groups are removed by catalytic hydrogenolysis). The solution is neutralized and the O→N migration can then proceed as before; the remaining O-acyl groups are removed as before; and the product is isolated as before described. This affords a 3",6'-di-N-actylated-kanamycin A or a 2',3",6'-tri-N-acylated-kanamycin B, respectively. In like manner, 3-N-benzylkanamycin A and 3-N-benzylkanamycin B can be converted into a 3",6'-di-N-acylated-3-N-benzylkanamycin A and 2',3"-6'-tri-N-acylated-3-N-benzylkanamycin B, respectively, via the sequence of: full N-protection; O-acylation; removal of the N protecting groups, O→N migration; and removal of any remaining O-acyl groups. In the case wherein R is hydroxy, at least 5 molar equivalents of acylating agent are required for the O-acylation step; in the case wherein R is amino, at least 4 molar equivalents of acylating agent are required for the acylation step.

3-N-Benzylkanamycin A and 3-N-benzylkanamycin B can be prepared by reductive alkylation of kanamycin A or kanamycin B with benzaldehyde under carefully controlled pH conditions. When kanamycin A or B in aqueous solution is subjected to reductive alkylation at room temperature or below, with a slight excess of benzaldehyde in the presence of sodium cyanoborohydride and the pH of the solution is carefully adjusted to 6, then the major product from the reaction is 3-N-benzyl-kanamycin A or 3-N-benzylkanamycin B, respectively. Minor amounts of the other N-substituted isomers and polysubstituted products are also produced in the reaction but these can be separated by conventional ion-exchange chromatography. The main fraction isolated from the column by elution with ammonium hydroxide is 3-N-benzyl-kanamycin A or 3-N-benzylkanamycin B, contaminated with a minor amount of the 1-N-benzyl isomer. In practice, this product is sufficiently pure to use directly in the process of the invention although, naturally, the 1-N-benzyl isomer present will lead, after acylation, O→N migration and deprotection, to the formation of the 1-N-benzylated isomer as a minor component together with the required 3-N-benzylated product of formula I.

As indicated hereinbefore, the compounds of the formula I are useful for the preparation of 1-N-substituted kanamycin A and kanamycin B derivatives. In particular, the compounds of the formula I, wherein $R^2$, $R^3$, $R^4$ and $R^5$ are as defined previously, can be used to prepare 1-N-[(S)-4-amino-2-hydroxybutyl]-kanamycin A and 1-N-[(S)-4-amino-2-hydroxybutyl]kanamycin B, the latter compounds being valuable by virtue of their outstanding antibacterial activity (West German Offenlegungsschrift No. 2,547,738). The said 1-N-[(S)-4-amino-2-hydroxybutyl] derivatives can be prepared from the compounds of the formula I in a variety of ways. However, a particularly convenient method involves: (i) reductive alkylation of a compound of the formula I with 3-benzyl-6-(S)-dihydroxymethyltetrahydro-1,3-oxazin-2-one (III); followed by (ii) basic hydrolysis to open the oxazine ring and remove the acyl groups $R^3$ and $R^5$ (and $R^6$, if $R^4$ is $R^6NH$); followed by (iii) catalytic hydrogenolysis to remove the benzyl group in the side chain at N-1 (and also the benzyl group at N-3 if $R^2$ is benzyl).

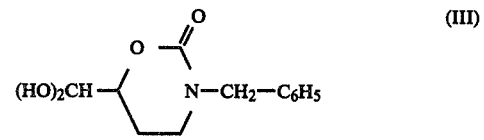

(III)

In step (i), the compound of the formula I is usually contacted with about 1 molar equivalent of the compound of the formula III and then the adduct so formed is reduced using sodium borohydride or sodium cyanoborohydride. The reaction is usually carried out in a reaction-inert solvent, such as aqueous N,N-dimethylformamide, at a pH of about 4 to 7, and at a temperature of about 25° to about 80° C.

Step (ii) is achieved by a hydrolysis reaction in which the product of step (i) is preferably treated with aqueous base. The reaction is conveniently performed with the product of step (i) dissolved in a reaction-inert solvent, e.g. water, aqueous methanol, aqueous ethanol, aqueous dioxan, aqueous tetrahydrofuran or the like, and can be effected using an alkali metal hydroxide or an alkaline earth metal hydroxide, such as sodium, potassium or barium hydroxide. The reaction can be performed at a temperature from about 0° C. to about 100° C., and it takes up to 5 days, depending upon the particular nature of the reactants and the temperature employed. It is found that, when the reaction is performed using 1N sodium hydroxide solution to effect the hydrolysis and the acyl group is formyl, the reaction is substantially complete within 48 hours at room temperature. The product can conveniently be isolated by neutralizing the solution and evaporation. The crude product can then be further purified, if desired, by conventional means, for example by ion-exchange chromatography.

In step (iii), the benzyl group in the N-1 side chain (and the benzyl group at N-3 if present) can be removed by catalytic hydrogenolysis. The removal of the benzyl group or groups can be achieved by subjecting the product of step (ii) to catalytic hydrogenation, in a suitable solvent such as a mixture of water, methanol and acetic acid, at 60 p.s.i., for several hours at about 60° C. When the reaction is complete the reaction mixture is worked up in conventional manner, e.g. by filtration and evaporation of the solvent. The crude product can then be purified if desired in the usual way, e.g. by recrystallization from a suitable solvent or by chromatography.

In addition to the above, if $R^3$ and $R^5$ (and $R^6$ if $R^4$ is $R^6NH$) are a very labile acyl group, such as trifluoroacetyl, the compounds of the formula I can be used to prepare 1-N-[$\omega$-amino-2-hydroxyalkanoyl] derivatives of kanamycins A and B. Thus, the compound of the formula I is reacted with the N-hydroxysuccinimide ester of an (S)-$\omega$-benzyloxycarbonylamino-2-hydroxyalkanoic acid. The reaction is suitably carried out with the reactants dissolved in an inert organic solvent, for example tetrahydrofuran, and is conveniently performed by adding a solution of the active ester to a solution of the kanamycin derivative at 0° C. The reaction can be monitored by thin layer chromatography and more active ester added if desired to ensure complete reaction. The reaction is conveniently allowed to proceed at room temperature and under these conditions acylation is substantially complete within 48 hours. The product is isolated by evaporation of the solvent and the product may be purified at this stage, if desired, by conventional techniques (e.g. crystallization or chromatography), but is more conveniently used in crude form in the next step of the process. Removal of the N-trifluoroacetyl groups is achieved by mild base hydrolysis and this may be performed by simply dissolving the product from the first step of the process is 1N ammonium hydroxide and allowing the solution to stand for several hours (e.g. overnight) at room temperature. Finally the benzyl and benzyloxycarbonyl groups may be removed together by catalytic hydrogenolysis by the method described previously 1-N-[$\omega$-Amino-2-hydroxyalkanoyl] derivatives of kanamycins A and B are known antibacterial agents (U.S. Pat. Nos. 3,781,268; 3,886,139 and 3,904,597).

The following examples and preparations are given solely for the purpose of further illustration. Thin layer chromatography was performed on silica plates using the solvent system stated. The spots were visualized after drying the plates by spraying with a 5% solution of t-butyl-hypochlorite in cyclohexane, drying the plates at 100° C. for 10 minutes in a ventilated oven cooling and spraying with starch-potassium iodide solution. Temperatures are given in ° C. "Amberlite" is a Registered Trade Mark, and refers to a cationic ion-exchange resin having a polystyrene matrix cross-linked with 3–5% of divinylbenzene which has then been sulfonated.

EXAMPLE I

3″,6′-Di-N-trifluoroacetylkanamycin A

Trifluoroacetic anhydride (5.0 ml.) was added slowly to a stirred solution of kanamycin A (1.0 g.) in trifluoroacetic acid (40 ml.) at 0°. The solution was allowed to stand at 0°–4° for 20 hours. The solvent was then evaporated under vacuum and the residue was treated with toluene (10 ml.) and evaporated to dryness. The trifluoroacetate salt was dissolved in dry tetrahydrofuran and neutralized by slowly adding to a stirred suspension of excess anhydrous potassium carbonate in tetrahydrofuran. The mixture was stirred at room temperature for 20 minutes and the suspension was then filtered and the filtrate evaporated to dryness. The product was dissolved in methanol (20 ml.) and kept at room temperature for 30 minutes. The solvent was evaporated under reduced pressure and the residue was chromatographed on silica, eluting with a solvent gradient of chloroform-methanol (3:1) to chloroform-methanol-17% ammonium hydroxide (8:4:1) to give 3″,6′-di-N-trifluoroacetylkanamycin A hydrate (0.52 g.) was a white hygroscopic solid. Rf 0.7 in methanol, chloroform, 17% ammonium hydroxide 4:1:1 (kanamycin A gave an Rf of 0.05). $\nu c = o$ 1665 cm$^{-1}$.

A sample was converted to the volatile di-N-acetyl-hepta-O-trimethylsilyl derivative as described in Preparation A. m/e found 1264. $C_{47}H_{94}N_4O_{15}F_6Si_7$ requires m/e 1264.

EXAMPLE II

3-N-Benzyl-3″,6′-di-N-trifluoroacetylkanamycin A

Trifluoroacetic anhydride (0.7 ml., 5 mmole) was added slowly to a solution of 3-N-benzylkanamycin A (0.23 g., 0.4 mmole) in trifluoroacetic acid (15 ml.) at 0°. The solution was kept at 0°–4° for 20 hours. The solvent was then evaporated and the residue treated with toluene (10 ml.) and evaporated to dryness. The product was dissolved in tetrahydrofuran (20 ml.) and slowly added to a stirred suspension of excess potassium carbonate in tetrahydrofuran. The suspension was stirred at room temperature for 30 minutes, filtered and the filtrate evaporated to dryness under reduced pressure. The residue was dissolved in methanol (20 ml.) and allowed to stand at room temperature for 30 minutes. The solvent was then removed under vacuum to yield 3-N-benzyl-3″,6′-di-N-trifluoroacetylkanamycin A Rf 0.5 in methanol-chloroform-8% ammonium hydroxide, 4:1:0.1 (3-N-benzylkanamycin A gave an Rf value of 0.01).

EXAMPLE III

3-N-Benzyl-3″,6′-di-N-acetylkanamycin A

Acetic anhydride (510 mg., 5 mmole) is added slowly to a solution of 3-N-benzylkanamycin A (0.23 g., 0.4 mmole) in trifluoroacetic acid (15 ml.) at 0°. The solution is kept at 0°–4° for 20 hours. The solvent is then evaporated and the residue treated with toluene (10 ml.) and evaporated to dryness. The product is dissolved in tetrahydrofuran (20 ml.) and slowly added to a stirred suspension of excess potassium carbonate in tetrahydrofuran. The suspension is stirred at room temperature for 30 minutes, filtered and the filtrate evaporated to dryness under reduced pressure. The residue is dissolved in methanol saturated with ammonia (20 ml.) and allowed to stand at room temperature for 2 hours. The solvent is removed under vacuum to yield crude 3-N-benzyl-3",6'-di-N-acetylkanamycin A, which is purified by chromatography using the procedure described in Example I.

EXAMPLE IV

The procedure of Example III is repeated, except that the acetic anhydride used therein is replaced by:
formic-acetic anhydride,
propionic anhydride,
valeric anhydride,
fluoroacetic anhydride,
difluoroacetic anhydride,
chloroacetic anhydride,
dichloroacetic anhydride,
trichloroacetic anhydride and
formic-acetic anhydride, respectively, and the 3-N-benzylkanamycin A is replaced by:
kanamycin A,
kanamycin A,
kanamycin B,
kanamycin A,
kanamycin B,
kanamycin A,
kanamycin A,
kanamycin B and
3-N-benzylkanamycin B respectively. This affords:
3",6'-di-N-formylkanamycin A,
3",6'-di-N-propionylkanamycin A,
2',3",6'-tri-N-valerylkanamycin B,
3",6'-di-N-fluoroacetylkanamycin A,
2',3",6'-tri-N-difluoroacetylkanamycin B,
3",6'-di-N-chloroacetylkanamycin A,
3",6'-di-N-dichloroacetylkanamycin A,
2',3",6'-tri-N-trichloroacetylkanamycin B,
3-N-benzyl-2',3",6'-tri-N-formylkanamycin B, respectively.

EXAMPLE V

3",6'-Di-N-acetylkanamycin A (A) A solution of 1,3,3",6'-tetra-N-benzyloxycarbonyl kanamycin A (*Bull. Chem. Soc. Japan*, 38, 1181 [1965]) (189.4 g.) in pyridine (568 ml.) and acetic anhydride (189 ml.) was stirred overnight at room temperature and then poured into water (1.9 liters). The aqueous solution was extracted with chloroform (1×1.8 liters and 1×1.0 liters) and the organic extract was evaporated to dryness under reduced pressure. Trituration of the residue with ether gave penta-O-acetyl-1,3,3",6'-tetra-N-benzyloxycarbonyl kanamycin A (224.8 g.) which was filtered and dried under vacuum. The product had m.p. 223°–229°; Rf 0.55 in chloroform-ethanol (12:1), δ 1.8–2.05 (15 proton multiplet, 5 acetyl groups) and 7.4 (20 proton singlet, 4 phenyl groups).

(B) A solution of penta-O-acetyl-1,3,3",6'-tetra-N-benzyloxycarbonyl kanamycin A (53 g.) in ethyl acetate (260 ml.) containing glacial acetic acid (260 ml.) was hydrogenated over 5% palladium on carbon (15 g.) at 60° and 50 p.s.i. for 7 hours. The solution was filtered and the filtrate was evaporated to dryness under reduced pressure. The residue was triturated with ether and the product penta-O-acetylkanamycin (32.9 g.) was collected and dried under vacuum, m.p. 97°–105°, Rf 0.0 in chloroform ethanol (12:1) compared to an Rf of 0.55 for the starting material. The proton magnetic resonance spectrum showed a complete absence of aromatic protons.

(C) A solution of penta-O-acetyl kanamycin A (139.2 g.) in methanol (1.4 liters) saturated with ammonia was allowed to stand overnight at room temperature and then evaporated to dryness under reduced pressure. The residue was dissolved in methanol (140 ml.) and the crude product was precipitated with chloroform (2.5 liters), filtered and dried in vacuum. The crude solid was slurried with ethanol (400 ml.) and the 3",6'-di-N-acetylkanamycin A (91.9 g.) was collected by filtration, washed with ether and dried under vacuum, m.p. 150°–180°, Rf 0.77 in methanol-0.880 ammonium hydroxide (1:1). It gave a $^{13}C$ n.m.r. spectrum and proton n.m.r. spectrum in full agreement with the required structure.

EXAMPLE VI

The procedure of Example V is repeated and the acylating agent used therein is:

formic-acetic anhydride,
propionic anhydride,
valeric anhydride,
fluoroacetic anhydride,
difluoroacetic anhydride,
chloroacetic anhydride,
dichloroacetic anhydride,
trichloroacetic anhydride,
methyl chloroformate,
butyl chloroformate and
benzoyl chloride, respectively, and the N-protected kanamycin derivative is:
1,3,3",6'-tetra-N-benzyloxycarbonylkanamycin A,
1,3,3",6'-tetra-N-benzyloxycarbonylkanamycin A,
1,2',3,3",6'-penta-N-benzyloxycarbonylkanamycin B,
1,3,3",6'-tetra-N-benzyloxycarbonylkanamycin A,
1,2',3,3",6'-penta-N-benzyloxycarbonylkanamycin B,
1,3,3",6'-tetra-N-benzyloxycarbonylkanamycin A,
1,3,3",6'-tetra-N-benzyloxycarbonylkanamycin A,
1,2',3,3",6'-penta-N-benzyloxycarbonylkanamycin B,
3-benzyl-1,3",6'-tri-benzyloxycarbonylkanamycin A,
3-benzyl-1,2',3",6'-tetra-N-benzyloxycarbonylkanamycin B and
1,3,3",6'-tetra-N-benzyloxycarbonylkanamycin A, respectively. This affords:
3",6'-di-N-formylkanamycin A,
3",6'-di-N-propionylkanamycin A,
2',3",6'-tri-N-valerylkanamycin B,
3",6'-di-N-fluoroacetylkanamycin A,
2',3",6'-tri-N-difluoroacetylkanamycin B,
3",6'-di-N-chloroacetylkanamycin A,
3",6'-di-N-dichloroacetylkanamycin A,
2',3",6'-tri-N-trichloroacetylkanamycin B,
3-benzyl-3",6'-di-N-methoxycarbonylkanamycin A,
3-benzyl-2',3",6'-tri-N-butoxycarbonylkanamycin B and
3",6'-di-N-benzoylkanamycin A, respectively.

EXAMPLE VII

2',3",6'-Tri-N-trifluoroacetylkanamycin B

Trifluoroacetic anhydride (3.6 ml.) was added slowly to a stirred solution of kanamycin B (960 mg., 2 mmole) in trifluoroacetic acid (50 ml.) at 0°. The solution was allowed to stand at 0°-4° for 20 hours. The solvent was then evaporated under reduced pressure and the residue treated with toluene (10 ml.) and evaporated to dryness. The trifluoroacetate salt was dissolved in tetrahydrofuran (30 ml.) and added slowly to a stirred solution of excess triethylamine in tetrahydrofuran. The solution was allowed to stand at room temerature for 40 minutes and the solvent was then evaporated under reduced pressure. The residue was dissolved in methanol to hydrolyze the remaining O-trifluoroacetyl groups and after 30 minutes at room temperature the solvent was evaporated under reduced pressure and the product was chromatographed on silica eluting with a solvent gradient of chloroform-methanol (3:1) to chloroform-methanol-17% ammonium hydroxide (20:10:1) to give 2',3",6'-tri-N-trifluoroacetylkanamycin B (452 mg., 29%) as a glass. Rf 0.70 in methanol-chloroform-8% ammonium hydroxide 4:1:0.1 (kanamycin B gave an Rf of 0.0).

The structure was confirmed by the following sequence of reactions: (a) Acetylation with acetic anhydride in methanol for 20 hours at room temperature followed by treatment with 1N ammonium hydroxide for 18 hours to remove the trifluoroacetyl groups gave a product containing two acetyl groups. m/e (field desorption) found 568, $C_{22}H_{41}N_5O_{12}$ requires M+1 568; (b) Treatment of this product with deuterioacetic anhydride in methanol at room temperature for 24 hours followed by reaction with a 2:1 mixture of hexamethyldisilazane and trimethylchlorosilane at room temperature for 24 hours gave the volatile tri-N-deuteroacetyl-di-N-acetyl-hexa-O-trimethylsilyl derivative. m/e found 1134, $C_{46}H_{86}N_5O_{15}D_9Si_6$ requires m/e 1134. Diacetylation was shown to have occurred on the 2-deoxy-streptamine ring from the fragmentation pattern, thereby confirming that trifluoroacetylation had initially taken place on the 2',3" and 6' positions in kanamycin B.

PREPARATION A

3-N-Benzylkanamycin A

Kanamycin A sulphate (24.3 g., 0.03 mole) was dissolved in water (150 ml.) and the pH adjusted to 6 by the dropwise addition of 5N hydrochloric acid. Sodium cyanoborohydride (1.95 g., 0.03 mole) was added and the mixture was cooled to 0° C. and stirred while a solution of benzaldehyde (3.61 g., 0.033 mole) dissolved in methanol (15 ml.) was added slowly over the course of 2½ hours. The mixture was allowed to warm to room temperature. After 16 hours the pH of the solution was adjusted to 5.5 by the addition of 1N hydrochloric acid and the solution was filtered and added to a column of Amberlite CG-50 ion-exchange resin in the ammonium-ion form. Elution first with water and then with a gradient of ammonium hydroxide of increasing concentration from 0–0.7N gave as major product 3-N-benzylkanamycin A contaminated with some 1-N-benzyl derivative (5.0 g., 28%) Rf 0.44 in methanol-chloroform-17% ammonium hydroxide 4:1:2. (Kanamycin A gave an Rf value of 0.15).

A sample was converted to the volatile tetra-N-acetyl-hepta-O-trimethylsilyl derivative by treatment with acetic anhydride in methanol at room temperature for 24 hours followed by reaction with a 2:1 mixture of hexamethyldisilazane and trimethylchlorosilane at room temperature for 24 hours. m/e found 1246. $C_{54}H_{106}N_4O_{15}Si_7$ requires m/e 1246.

The position of substitution was confirmed by the following sequence of reactions: (a) treatment with t-butyloxycarbonyl azide gave a compound containing three t-butyloxycarbonyl groups as well as the benzyl group (from n.m.r.), (b) hydrogenation to remove the benzyl group, (c) acylation with N-[(S)-4-benzyloxycarbonylamino-2-hydroxy-butyryloxy]succinimide, and (d) removal of the N-protecting groups by hydrogenation followed by treatment with trifluoroacetic acid gave, as major product, 3-N-[(S)-4-amino-2-hydroxybutyryl]-kanamycin A (BB-K29) identified by comparison with an authentic sample prepared according to the procedure of Naito et al., *Journal of Antibiotics,* 26, 297 (1973).

PREPARATION B

3-N-Benzylkanamycin B

The title compound is prepared using the procedure of Preparation A, but replacing the kanamycin A sulphate used therein by an equimolar amount of kanamycin B sulphate.

PREPARATION C

1-N-[(S)-4-Amino-2-hydroxybutyryl]kanamycin A (BB-K8)

3",6'-Di-N-trifluroacetylkanamycin A (prepared from 1.0 g. kanamycin A by the method of Example I) in tetrahydrofuran (40 ml.) was treated with N-[(S)-4-benzyloxycarbonylamino-2-hydroxy-butyryloxy]succinimide (1.08 g., 3.1 mmoles) in tetrahydrofuran (50 ml.). The solution was allowed to stand at room temperature for 24 hours, then a further 0.54 g. of N-[(S)-4-benzyloxycarbonylamino-2-hydroxy-butyryloxy]succinimide was added and the solution was kept at room temperature for a further 24 hours. The solvent was evaporated under vacuum and the residue was dissolved in 1N ammonium hydroxide and allowed to stand at room temperature for 20 hours. The solution was concentrated under vacuum and the product dissolved in a mixture of dioxan, water and acetic acid (55 ml., 5:5:1) and hydrogenated over 5% palladium on charcoal catalyst at 30° and 50 p.s.i. for 6 hours. The mixture was filtered and the filtrate evaporated. The residue was chromatographed on Amberlite CG-50 ion-exchange resin (NH₄+form) eluting with a gradient of ammonium hydroxide of increasing concentration from 0–0.5 N, to give the title compound (0.11 g., 9.2% from kanamycin A) identified by comparison with an authentic sample.

PREPARATION D

1-N-[(S)-4-Amino-2-hydroxybutyryl]kanamycin A

3-N-Benzyl-3",6'-di-N-trifluoroacetylkanamycin A (prepared from 0.23 g. 3-N-benzylkanamycin A as described in Example II) was treated directly with a solution of N-[(S)-4-benzyloxycarbonylamino-2-hydroxy-butyryloxy]-succinimide (0.017 g., 0.5 mmole) in tetrahydrofuran (15 ml.) at 0°. The solution was allowed to stand at room temperature for 24 hours. A further 0.35 g. of the active ester in tetrahydrofuran was then added and the solution kept for a further 20 hours at room temperature. The solution was concentrated under vacuum and the residue dissolved in a mixture of methanol, water and acetic acid (30 ml., 10:10:1) and hydrogenated over palladium on charcoal catalyst at 40° and 50 p.s.i. for 13.5 hours. The suspension was filtered and the filtrate evaporated. The product was purified by ion-exchange chromatography on Amberlite GC-50 (NH$_4$+form) as described in Preparation C, to yield the title product (84 mg., 36% from 3-N-benzylkanamycin A), identified by comparison with an authentic sample.

PREPARATION E

1-N-[(S)-4-Amino-2-hydroxybutyryl]kanamycin B

2',3'',6'-Tri-N-trifluoroacetylkanamycin B is reacted with N-[(S)-4-benzyloxycarbonylamino-2-hydroxybutyryloxy]succinimide in a similar manner to that described in Preparation C to give, after deprotection and purification, 1-N-[(S)-4-amino-2-hydroxybutyryl]kanamycin B (BB-K26).

PREPARATION F

1-N-[(S)-4-Amino-2-hydroxybutyl]kanamycin A

A solution of 3'',6'-di-N-acetylkanamycin A (2.84 g.) and 3-benzyl-6-(S)-dihydroxymethyl-tetrahydro-1,3-oxazin-2-one (1.305 g.) in dimethylformamide (28.4 ml.) was heated at 60° for one hour and then cooled to 30°. Sodium borohydride (0.189 g.) was added and the mixture was stirred for a further one hour. Water (1.0 ml.) was added, the mixture was allowed to stand overnight and the solvent was then removed under reduced pressure. The residue was heated with 3N sodium hydroxide solution (28.4 ml.) at 80° for 4 hours and, after cooling, the pH of the reaction mixture was adjusted to 5.7 with concentrated hydrochloric acid. The crude solution of 1-N-[(S)-4-benzylamino-2-hydroxybutyl]kanamycin A and 3-N-[(S)-4-benzylamino-2-hydroxybutyl]kanamycin A was passed down a column of Amberlite CG-50 ion-exchange resin (NH$_4$+form) eluting first with water to remove inorganics and then with 0.15 M ammonia to isolate the crude aminoglycoside mixture. The required column fractions were evaporated and the residue was dissolved in a mixture of methanol (15 ml.), acetic acid (15 ml.), and water (15 ml.) and hydrogenated over 30% palladium on carbon catalyst at 60° and 60 p.s.i. for 16 hours. The solution was filtered and the solvent removed under reduced pressure. The product was purified by ion-exchange chromatography to yield 1-N-[(S)-4-amino-2-hydroxybutyl]kanamycin A (0.5 g.) identified by comparison with an authentic sample.

PREPARATION G

3-Benzyl-6(S)-dihydroxymethyltetrahydro-1,3-oxazin-2-one (A) A solution of benzylamine (2.14 g., 0.02 moles) in water (25 ml.) was adjusted to pH 5 with 5N hydrochloric acid. 2-Deoxy-D-ribose (1.34 g., 0.01 mole) and sodium cyanoborohydride (0.062 g., 0.01 mole) were added and the solution was allowed to stand for 15 hours at room temperature. The pH of the solution was adjusted to 10 with sodium carbonate and the mixture was washed several times with ethyl acetate. The aqueous solution was cooled to 0° C., and phenyl chloroformate (1.7 g., 0.011 mmoles) in dioxan (15 ml.) was added with stirring. After 3 hours at 0° C., the reaction was allowed to warm to room temperature, the pH was adjusted to 7 by the addition of 5N hydrochloric acid and the mixture was extracted with ethyl acetate. The organic extract was dried over magnesium sulphate and evaporated under reduced pressure to yield 1,2(S), 3(S)-trihydroxy-5-[N-phenoxycarbonyl-N-benzylamino]-pentane (2.1 g.) as an oil which slowly solidified on standing. δ(CDCl$_3$+D$_2$O) 7.2 (10H, m); 4.5 (2H, s); 3.5 (6H, m) 1.8 (2H, m). ν$_{max.}$ (film) 3400, 1705, 1600 cm$^{-1}$.

(B) The product from A (1.5 g.), dissolved in a mixture of t-butanol (50 ml.) and dioxan (50 ml.), was stirred at room temperature and treated with sodium hydride (0.34 g., as 70% dispersion in oil). After 24 hours the pH was adjusted to 7 with 5N hydrochloric acid and the solution was evaporated to dryness. The product was extracted with ethanol and the inorganic residue was discarded. Repeated evaporation and extraction into ethanol gave a product free from inorganic material. The residue was finally partitioned between ethyl acetate and water and the aqueous layer was separated and evaporated under reduced pressure to yield 3-benzyl-6-(S)-(1',2'-dihydroxyethyl)tetrahydro-1,3-oxazin-2-one (0.3 g.) as an oil. δ(D$_2$O) 7.3 (5H, s); 4.4 (2H, s); 4.2 (1H, m); 3.7 (3H, m); 3.1 (2H, m); 1.9 (2H, m). ν$_{max.}$ (film) 3400, 1660 cm$^{-1}$.

(C) The product from B (0.2 g.) in water (10 ml.) was treated with an aqueous solution of periodic acid (0.2 g.), taken to pH 5 with 5N sodium hydroxide at room temperature. After a few minutes a precipitate formed and then the reaction mixture was allowed to stand for 2 hours. The solid precipitation was then collected by filtration, washed with a little water and dried to yield 3-benzyl-6(S)-dihydroxymethyl-tetrahydro-1,3-oxazin-2-one (0.15 g.), m.p. 120° C. (Found: C, 60.0; H, 6.3; N, 5.8. C$_{12}$H$_{15}$NO$_4$ requires C, 60.7; H, 6.3; N, 5.9%). δ(DMSO-d$_6$) 7.3 (5H, s); 6.1 (2H, d, exchangeable with D$_2$O); 4.9 (1H, m); 4.5 (2H, s); 4.0 (1H, m); 3.2 (2H, m); 2.0 (2H, m). ν$_{max.}$ 3300, 1670 cm$^{-1}$ [α]$_D$+71.5° (C, 1 in methanol).

What is claimed is:
1. A compound of the formula

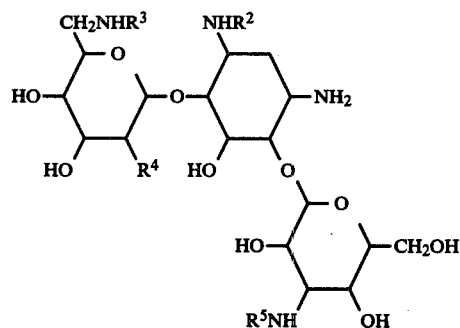

wherein
R$^2$ is selected from the group consisting of hydrogen and benzyl;
R$^4$ is selected from the group consisting of hydroxy and R$^6$NH;
and R$^3$, R$^5$ and R$^6$ are each selected from the group consisting of formyl, alkanoyl having from 2 to 5 carbon atoms, fluoroacetyl, difluoroacetyl, trifluoroacetyl, chloroacetyl, dichloroacetyl, trichloroacetyl, alkoxycarbonyl having from 2 to 5 carbon atoms and benzoyl;

provided that $R^3$, $R^5$ and $R^6$ are always the same.

2. A compound according to claim 1, wherein $R^2$ is hydrogen.

3. A compound according to claim 2, wherein $R^4$ is hydroxy.

4. The compound according to claim 3, wherein $R^3$ and $R^5$ are each formyl.

5. The compound according to claim 3, wherein $R^3$ and $R^5$ are each acetyl.

6. The compound according to claim 3, wherein $R^3$ and $R^5$ are each trifluoroacetyl.

7. The compound according to claim 2, wherein $R^4$ is $R^6NH$ and $R^3$, $R^5$ and $R^6$ are each trifluoroacetyl.

8. A process for the preparation of a compound of the formula

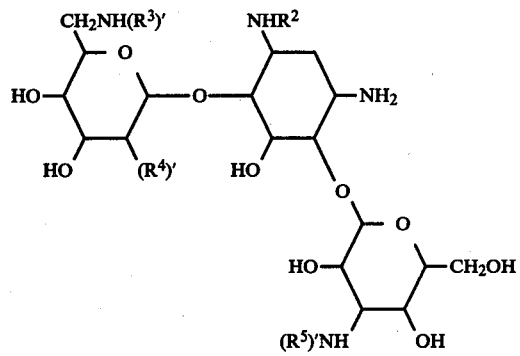

wherein
  $R^2$ is selected from the group consisting of hydrogen and benzyl;
  $(R^4)'$ is selected from the group consisting of hydroxy and $NH(R^6)'$;
  and $(R^3)'$, $(R^5)'$ and $(R^6)'$ are each selected from the group consisting of formyl, alkanoyl having from 2 to 5 carbon atoms, fluoroacetyl difluoroacetyl, trifluoroacetyl, chloroacetyl, dichloroacetyl and trichloroacetyl;
  provided that $(R^3)'$, $(R^5)'$ and $(R^6)'$ are always the same; which comprises:
  (a) reacting a comound of the formula

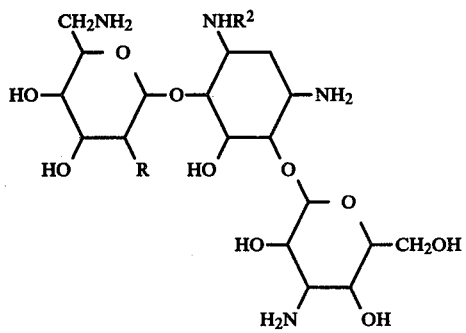

wherein R is selected from the group consisting of hydroxy and amino and $R^2$ is selected from the group consisting of hydrogen and benzyl, with an excess of formic-acetic anhydride or $(R^7CO)_2O$, in a reaction-inert solvent, at a pH below about 5 to achieve selective O-acylation of the reactive hydroxy groups, wherein $R^7$ is selected from the group consisting of alkyl having from 1 to 4 carbon atoms, fluoromethyl, difluoromethyl, trifluoromethyl, chloromethyl, dichloromethyl and trichloromethyl;

(b) neutralizing a solution of the product of step (a), in a reaction-inert organic solvent, and at a temperature of from about 0° to about 50° C., to achieve O→N acyl migration; and (c) hydrolyzing the product of step (b) at a temperature of from about 0° to about 100° C., to remove any remaining O-acyl groups.

9. The process according to claim 8, wherein R and $(R^4)'$ are each hydroxy, $R^2$ is hydrogen and $(R^3)'$ and $(R^5)'$ are each trifluoroacetyl, and the reaction-inert solvent used in step (a) is trifluoroacetic acid.

10. A process for the preparation of a compound of the formula

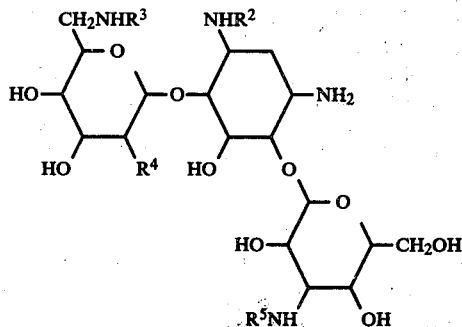

wherein
  $R^2$ is selected from the group consisting of hydrogen and benzyl;
  $R^4$ is selected from the group consisting of hydroxy and $NHR^6$;
  and $R^3$, $R^5$ and $R^6$ are each selected from the group consisting of formyl, alkanoyl having from 2 to 5 carbon atoms, fluoroacetyl, difluoroacetyl, trifluoroacetyl, chloroacetyl, dichloroacetyl, trichloroacetyl, alkoxycarbonyl having from 2 to 5 carbon atoms and benzoyl;
  provided that $R^3$, $R^5$ and $R^6$ are always the same; which comprises:
  (i) reacting a comound of the formula

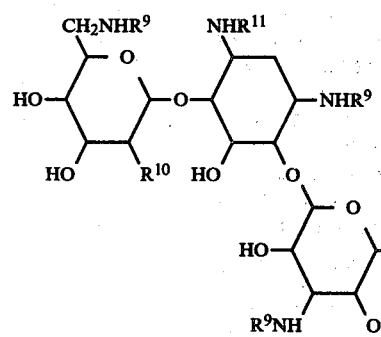

wherein $R^9$ is benzyloxycarbonyl; $R^{10}$ is selected from the group consisting of hydroxy and $NHR^9$; and $R^{11}$ is selected from the group consisting of benzyl and $R^9$, with an excess of formic-acetic anhydride, $[(R^7)'CO]_2O$, $(R^7)'$—CO—Cl or $R^8$—CO—Cl, in a reaction-inert solvent to achieve O-acylation of all the reactive hydroxy groups, wherein $(R^7)'$ is selected from the group consisting of alkyl having from 1 to 4 carbon atoms, fluoromethyl, difluoromethyl, trifluoromethyl, chloromethyl, dichloromethyl, trichloromethyl, and phenyl; and $R^8$ is alkoxy having from 1 to 4 carbon atoms;

(ii) removing the amino protecting groups, (iii) neutralizing a solution of the product of step (ii), in a reaction-inert solvent, at a temperature of from about 0° to about 50° C., to achieve O→N acyl migration; and (iv) hydrolyzing the product of step (iii), at a temperature of from about 0° to about 100° C., to remove any remaining O-acyl groups.

11. The process according to claim 10, wherein $R^4$ and $R^{10}$ are each hydroxy, $R^2$ is hydrogen, $R^3$ and $R^5$ are each acetyl and $R^{11}$ is benzyloxycarbonyl; and step (i) is carried out using $[(R^7)'CO]_2O$, wherein $(R^7)'$ is methyl.

* * * * *